United States Patent
Matak et al.

(10) Patent No.: US 11,013,464 B1
(45) Date of Patent: *May 25, 2021

(54) ATHLETIC-WEAR HAVING INTEGRAL MEASURING SENSORS

(71) Applicant: Mayfonk Athletic, LLC, Ft. Lauderdale, FL (US)

(72) Inventors: Martin T. Matak, Plantation, FL (US); Jef Spaleta, Fairbanks, AK (US)

(73) Assignee: Mayfonk Athletic, LLC, Ft. Lauderdale, FL (US)

( * ) Notice: Subject to any disclaimer, the term of this patent is extended or adjusted under 35 U.S.C. 154(b) by 231 days.

This patent is subject to a terminal disclaimer.

(21) Appl. No.: 16/206,719

(22) Filed: Nov. 30, 2018

Related U.S. Application Data

(60) Continuation of application No. 16/125,023, filed on Sep. 7, 2018, which is a continuation of application No. 15/284,027, filed on Oct. 3, 2016, now Pat. No. 10,070,817, which is a continuation of application No. 14/511,873, filed on Oct. 10, 2014, now Pat. No. 9,456,785, which is a continuation of application No. 13/591,895, filed on Aug. 22, 2012, now Pat. No. 8,860,584, which is a division of application No. 12/429,246, filed on Apr. 24, 2009, now Pat. No. 8,253,586.

(51) Int. Cl.
*A61B 5/00* (2006.01)
*H04Q 9/00* (2006.01)
*G06F 17/00* (2019.01)
*G01L 5/00* (2006.01)

(52) U.S. Cl.
CPC .......... *A61B 5/6807* (2013.01); *G01L 5/0095* (2013.01); *G06F 17/00* (2013.01); *H04Q 9/00* (2013.01); *H04Q 2209/75* (2013.01)

(58) Field of Classification Search
CPC ...................................................... G04B 47/00
USPC .................................................... 340/870.07
See application file for complete search history.

(56) References Cited

U.S. PATENT DOCUMENTS

| 7,693,668 B2 * | 4/2010 | Vock | G01C 9/00 |
| | | | 702/44 |
| 10,070,817 B1 * | 9/2018 | Matak | G01L 5/0095 |

* cited by examiner

*Primary Examiner* — Dharti H Patel
(74) *Attorney, Agent, or Firm* — Duane Morris LLP

(57) ABSTRACT

A computer implemented method comprises receiving, during a sporting event, raw data at a processor connected to a fantasy sports league network or gambling network. The raw data includes one or more athletic performance parameters that correspond to a physical movement of an athlete. The method further comprises computing in real time at the processor, during the sporting event, performance assessments for the athlete based on the athletic performance parameters. The performance assessments correspond specifically to an activity of the sporting event, and indicate a peak athletic performance parameter for the athlete. The method further comprises transmitting, during the sporting event, a signal from the processor to one or more subscriber devices connected to a fantasy sports league network or gambling network. The signal enables a display of the one or more performance assessments or athletic performance parameters on the subscriber devices.

50 Claims, 12 Drawing Sheets

ATHLETIC-WEAR HAVING INTEGRAL MEASURING SENSORS

CROSS REFERENCE TO RELATED APPLICATIONS

This application is a continuation of U.S. patent application Ser. No. 16/125,023 filed on Sep. 7, 2018, which is a continuation of U.S. patent application Ser. No. 15/284,027 filed on Oct. 3, 2016, now U.S. Pat. No. 10,070,817 issued Sep. 11, 2018, which is a continuation of U.S. patent application Ser. No. 14/511,873 filed on Oct. 10, 2014, now U.S. Pat. No. 9,456,785 issued Oct. 4, 2016, which is a continuation of U.S. patent application Ser. No. 13/591,895 filed on Aug. 22, 2012, now U.S. Pat. No. 8,860,584 issued Oct. 14, 2014, which is a divisional of U.S. patent application Ser. No. 12/429,246 filed on Apr. 24, 2009, now U.S. Pat. No. 8,253,586 issued Aug. 28, 2012, the entirety of each of the above is hereby incorporated herein by reference.

FIELD OF THE INVENTION

The present inventions relate generally to athletic-wear having electronic devices for measuring and displaying information, and more particularly to athletic-wear that includes integral electronic circuitry and sensors for measuring, processing and displaying the various parameters of an athlete's performance including real time display and data transmission.

BACKGROUND OF THE INVENTION

The footwear industry currently provides shoes and boots that include technology for measuring and monitoring certain aspects of individual or athletic performance. For example, pedometers have been incorporated in footwear for measuring the distance a person walks or runs based upon body motion and different theoretical mathematical calculations. Footwear also includes devices for measuring and remotely displaying personal and physiological parameters such as pulse rate, weight and calorie loss, body temperature and the like.

Particular references in the field include the U.S. Patent Applications Publication 2007/0021269 dated Jan. 25, 2007 to Shum entitled INTERFACES AND SYSTEMS FOR DISPLAYING ATHLETIC PERFORMANCE INFORMATION ON ELECTRONIC DEVICES, which discusses an athletic performance monitoring system for measuring athletic performance data and displaying the desired information in a variety of manners. The sensors 102(a)-102(d), can be placed in or about the shoe, wrist-bands, and/or articles of clothing. The sensors detect physical or physiological conditions, and transmit that information for electronic processing and display on units such as LCD's, LED's or plasma screens. This reference discusses displaying information for pedometer type speed and/or distance measure outlets, GPS data, step impact force, jump height data, pulse rate, body temperature, blood pressure and hydration levels. Also, the patent application discloses athletic performance monitoring systems including components for sensing performance data and/or displaying desired information to users. Electronic interface systems facilitate transfer of the data from the performance sensing system to a display device, e.g., to enable the display of athletic performance data on an electronic display device, including conventional electronic display devices that are known and commercially available (e.g., cellular telephones, PDAs, pagers, beepers, MP3 or other audio players, radios, portable televisions, portable DVD players, other video playing devices, watches, etc.). The sensing systems, as well as any data transfer systems associated therewith, may be included as part of an article of footwear, an article of clothing, a piece of athletic equipment, or the like, or even included as part of the interface device.

U.S. Patent Application Publication 2007/0011919 dated Jan. 18, 2007 issued to Case, Jr. is entitled SYSTEMS FOR ACTIVATING AND/OR AUTHENTICATING ELECTRONIC DEVICES FOR OPERATION WITH FOOTWEAR AND OTHER USES and is directly related to the '269 publication. This publication addresses the actual specific sensors and systems for activating the electronic devices in conjunction with the footwear or other articles of clothing.

Note FIGS. 3(A), 4 and 6 which depict the sensor unit 102 being place about the sole of the footwear. Various methods are discussed for activating and/or deactivating the detachable module from the clothing or footwear, different algorithms for calculating various data, as well utilizing light sources, magnets and magnetic sensing systems, and RFID systems. There is also an integrity aspect to these first two disclosures, in which authentication and authorization confirmations are calculated. Both references focus on how the module is removeably secured to the footwear, and how there is a dual activation system used in conjunction with the module. The module can be attached utilizing straps, flaps, Velcro type fasteners or the like. Additionally, the application discloses articles of footwear and footwear systems including modules, e.g., for sensing physical and/or physiological characteristics associated with use of the footwear or for performing other functions. Such systems and methods may use physical or other interaction(s) between the module and the article of footwear for activating and/or deactivating the module and/or sensing devices included with the module, for confirming whether the module and footwear are authorized for use with one another, and/or for automatic data algorithm selection methods. Additionally, such systems and methods also may use the activation and/or authentication systems for the module for data input to the module. Some examples of such systems and methods may utilize magnets and magnetic sensing systems and/or light (or other radiation) sources and sensing systems for activation, authentication, data input, and/or algorithm selection.

U.S. Pat. No. 7,200,517 issued on Apr. 3, 2007 to Darley et al. is entitled MONITORING ACTIVITY OF A USER IN LOCOMOTION ON FOOT discloses a specially designed mount which is removable attached underneath the shoelace of a shoe, and incorporates a tongue and groove mount and housing system. The device senses motion of the shoe, and determines physiological parameters as well as pedometer readings. Complex software and mathematical calculations are used to determine distance, heart rate, speed and altitude. The patent discloses an apparatus comprising a mount, a housing, and a sensor. The mount is adapted to be disposed at least partially underneath a shoelace of a shoe. The housing is configured and arranged in at least first and second states in relation to the mount, wherein in the first state the housing is movable with respect to the mount and in the second state the housing is immovable with respect to the mount. There is a tongue on one of the mount and the housing and a groove on the other of the mount and the housing, the tongue being adapted to engage the groove when the housing is in the second state in relation to the mount and to disengage the groove then the housing is in the first state with respect to the mount.

U.S. Pat. No. 7,171,331 issued on Jan. 30, 2007 to Vock et al. is entitled SHOES EMPLOYING MONITORING DEVICES, AND ASSOCIATED METHODS and illustrates specially designed accelerometers used with sensors which calculate speed or distance traveled, among several other end uses. Note FIGS. 36, 37 and 61, which disclose multiple sensors being incorporated into each respective shoe, wherein time differentials received between shoes are used to calculate distance and speed. Additionally, methods are disclosed for determining speed or distance traveled of moving persons by utilizing sensors selectively insertable within shoes. Shoe based systems employing sensors (e.g., accelerometers) are disclosed to determine and report (e.g., via a watch or MP3 player) speed and/or distance traveled.

Japanese Patent Publication JP20004121267 dated Apr. 22, 2004, issued to Kiyoshi is entitled STEP DETECTOR, FRONT STEP SEARCHING SYSTEM AND TRAFFIC CONTROL SYSTEM relates to a step detector and front searching mechanism for shoe wear. The abstract indicates that sensors and ultrasonic transmitters are used to measure the forward distance to an object, as well as the height of the road surface from the shoe bottoms. The technology is used to assist those people who are vision impaired or blind, and to control the flow of traffic in the vicinity.

U.S. Pat. No. 4,703,445 "ATHLETIC SHOE FOR RUNNING DISCIPLINES AND A PROCESS FOR PROVIDING INFORMATION AND/OR FOR EXCHANGING INFORMATION CONCERNING MOVING SEQUENCES IN RUNNING DISCIPLINES" discloses an athletic shoe system for running disciplines and a process for emitting and/or exchanging information concerning movement factors of running disciplines enabling the athlete to always be sufficiently informed regarding his/her training program that is in progress or completed. In particular, in an area of the sole that is less stressed during use, at least one free space is provided where a transmitter is housed which, via a sensor provided in the sole, can emit at least one output signal. In accordance with preferred embodiments, a transmitter in a first shoe of a pair of shoes receives the signals from the sensor and transmits emissions in correspondence with their receipt.

U.S. Pat. No. 5,452,269 "Athletic Shoe with Timing Device" discloses an athletic shoe that includes a timing device for measuring the amount of time the athletic shoe is off the ground and in air. The athletic shoe can also include a notification device that can be operatively coupled to the timing device for notifying a wearer of the athletic shoe of a message. The message can include information related to the amount of time the athletic shoe is off the ground and in the air.

U.S. Pat. No. 5,720,200 "Performance Measuring Footwear" discloses a foot mounted apparatus for measuring one or more locomotive performance parameters of a person. Such locomotive performance parameters preferably include user vertical leap time, user vertical jump distance, user walking or running speed, user trip distance traveled, and accumulated total lifetime distance traveled by the apparatus. It is preferred that the apparatus include all of the structures of an athletic shoe such as a sole, upper, tongue, and lace. Four membrane switches are located in the sole of the footwear: a pair of membrane switches is positioned under the ball of the user's foot and a pair of membrane switches is positioned under the heel of the user's foot. The membrane switches sense the compressive pressure of the foot on the sole and detect when the foot leaves and contacts the underlying surface. A microprocessor calculates a performance parameter for the person based upon the elapsed time between the foot push off and the foot strike.

U.S. Pat. No. 7,054,784 "Sport Monitoring Systems" discloses methods and systems for determining speed, power and/or impact (sporting characteristics) of persons involved in activity. Wireless signals may be generated indicative of the sporting characteristics for receipt and display on a watch worn by the user or on a remote display. Sensors may attach to the person or to a vehicle ridden by the person, to gauge activities such as jogging, hockey, biking, football and aerobics.

The remaining general state of the art relates to pedometers, apparatus mounted within or around shoes, skis, boots or lofted vehicles, along with location and tracking systems. These generally disclose a variety of systems utilizing activation switches, microprocessors, electronic circuits, and software to process and calculate desired monitoring conditions. These include loft or air time, distances traveled and terrain encountered, and impact conditions. Many different sensors, receiver/transmitters, display units, wrist and head bands are discussed. Some references use loft time to calculate the height of jumps with correction factors.

SUMMARY OF THE INVENTION

A performance measuring system integrated with an article of clothing, the system comprising a computing unit means for coordinating, processing and transmission of sensor data connected to a bus means and an antenna means; a sensor means for measuring performance characteristics connected to the bus means; a bus means for facilitating transmission and reception of control and data values between the computing unit means and the sensor means; and an antenna means connected to the computing unit means for communicating with other computing devices and transmission of sensor data. The other computing devices display the sensor data to a user or forward the sensor data onto another communication media such as the internet or interactive television.

In another embodiment there is a social networking system for the sharing of athletic statistics comprising a webservice accessible via an internet; a personal processing unit that is selectively connectible to the webservice through user interaction and that is also loaded with a client computing software; a computing unit having an activity program for at least one sensor and the computing unit connected to at least one sensor device that is selectively connectible to the personal processing unit through user interaction. This social networking system further comprises an activity update service integrally associated with the webservice wherein the activity update service transfers updates to the computing unit through communication via the internet and across the personal processing unit.

BRIEF DESCRIPTION OF THE SEVERAL VIEWS OF THE DRAWINGS

The invention may be better understood by reference to the drawings as described below.

DETAILED DESCRIPTION OF THE INVENTION

The following is detailed description of the invention as described by the accompanying drawings.

The instant invention has evolved greatly from a "VERT™" technology that measured the vertical leap of the wearer of a shoe into a much broader and more resplendent "All in One Training" modular technology known as the "Mayfunk." This new and enhanced vision is designed to track one or more of an athlete's performance in any sport and deliver real-time data on personal computing devices such as a generic Personal Processing Units (PPUs), PDAs, mp3 players or other audio players, cell phones, pagers, beepers, radios, portable televisions, portable DVD players, other video playing devices, calculators, watches etcetera, and or non-personal computing devices such as networked computers, broadcast TV or one or more social websites. Using the new Mayfunk technology requires data measuring one or more athletic performance parameters to be uploaded or transmitted from the onboard sensor system to the generic PPUs, PDAs, mp3 players, cell phone etcetera, and or non-personal computing devices such as a networked computer, broadcast TV or a social website.

Examples of the athletic performance parameters to be transmitted include but are not limited to acceleration, cadence, distance, GPS, vertical leap, heart rate, pace, pressure, contact, speed, swing plane, temperature, time and many more. All data is transmitted in real-time to a main personal processing unit (PPU) or to a device (PDAs, mp3 players, cell phone) that has the ability to transmit or download the sensor information to other personal and non-personal devices. The so-called PPU is simply an athletic performance parameter dedicated computing device that is empowered to download the performance data as described above. It is similar to a PDA, cell phone, mp3 player in size and carries within it the Mayfunk software that is capable of receiving and processing the sensor data. Then the athletic parameter that has been so measured, processed and recorded in an onboard small memory unit can be transmitted to other personal and non-personal units if so desired by the owner of the PPU inputting a set of keystrokes, button pressing or touching the screen if the PPU is so equipped.

Figure 1:
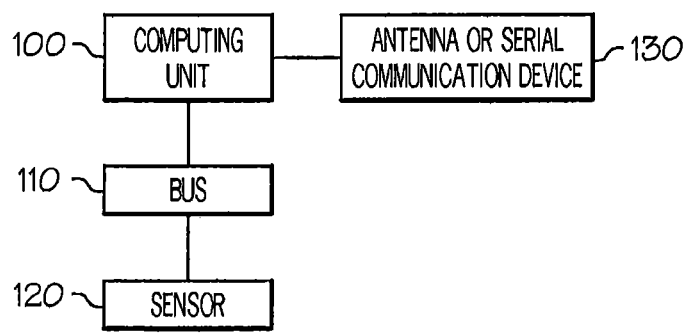
FIG. 1 is a system level view of the instant invention that is to be integrated with an article of clothing such as a shoe, glove or other such item as taught by the invention.

FIG. 1 is a system level view of the instant invention that is to be integrated with an article of clothing such as a shoe, glove, wrist band, hat, shorts, cap, shirt, helmet, pads, pants, or other such item as taught by the invention. The system comprises a computing unit 100 (a controller, microcontroller, ARM microcontroller) that communicates over a bus 110 with a sensor device 120; the computing unit 100 also has within itself a short-term memory. Additionally, an antenna 130 that transmits some form of electromagnetic radiation is connected with the computing unit 100. The computing unit 100 monitors the athletic performance parameters via bus 110 (serial, parallel, Bluetooth, USB, I2c, generic bus) that are being measured utilizing sensor 120. Examples of the athletic performance parameters to be measured include but are not limited to acceleration, cadence, distance, GPS, vertical leap, heart rate, pace, pressure, contact, speed, swing plane, temperature, time, a generic athletic performance parameter and many more. The computing unit 100 having sensed some real time data has the capability to process that data in real time as well as to process the data to obtain desirable quantities, for example, peak performance data such as the maximum height having been jumped by an athlete. The computing unit 100 also provides period data for extended periods of time such as 1, 5, 10, 20 seconds etcetera. All of this information is transferable from computing unit 100 utilizing antenna 130 to another personal computing device (not shown) or onto a network or to non-personal devices (not shown). The antenna unit 130 communicates via Bluetooth technology to a PPU or alternatively communicates through a USB mechanical connection. Alternatively, the computing unit 100 can communicate via Wifi or other type of electromagnetic communication to a networked web site as described below. Power is provided either from a wall outlet socket in the article of clothing or from one or more batteries contained in the article of manufacture.

Figure 2:
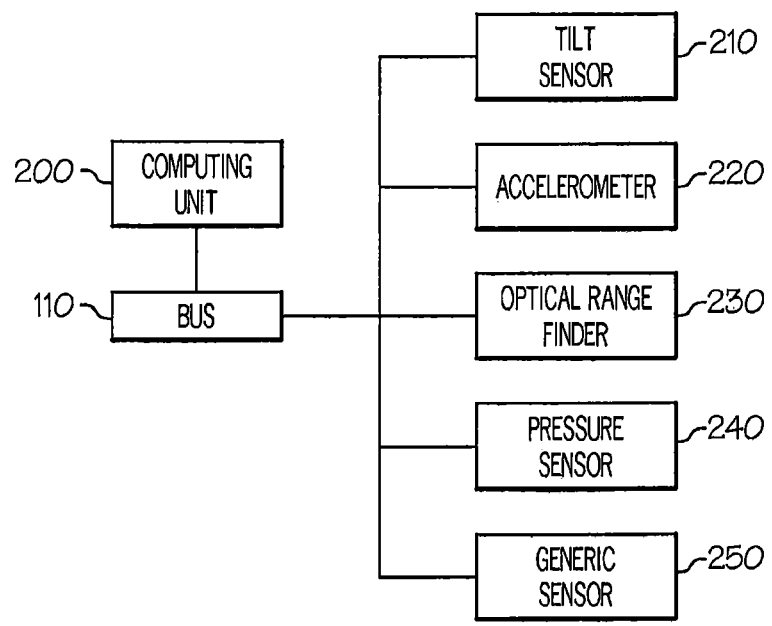
FIG. 2 is a graphical illustration of the range of sensors that singly or in any combination may be integrated into an article of clothing such as a shoe, glove or similar item as taught by the invention.

FIG. 2 is a graphical illustration of the range of sensors that singly or in any combination may be integrated into an article of clothing such as a shoe, glove or similar item as taught by the invention. Computing unit 200 that is integrated onboard the article of clothing is capable of communicating with a variety of different types of sensor units.

Some of the sensor units that computing unit 200 is able to communicate with are shown in FIG. 2. These include but are not limited to a tilt sensor 210, an accelerometer 220, an optical range finder 230, a pressure sensor 240 and a generic sensor 250. Other types of sensor can include but are not limited to laser, laser diode, and sound sensors. In this invention the words 'integrated' or 'onboard' when used in connection with the disposition of items on the clothing are used interchangeably and mean that there is a unit that has been placed in the ordinary surface or interior of an item so as not to cause undue distortion of the article of clothing's ordinary purpose. Additionally, the onboard computing unit 200 is detachable from the article of clothing and modularized as taught with reference to FIG. 3.

Figure 3A:
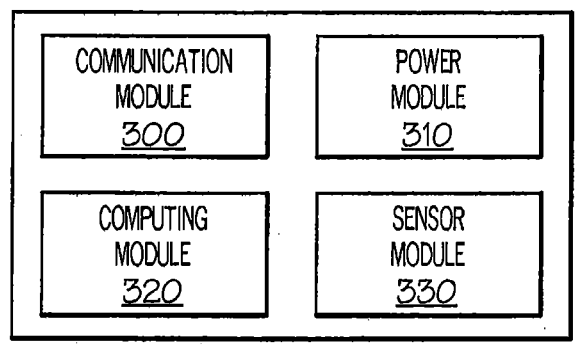
FIG. 3A is a graphical representation of a first view of the modularization choices as taught by the instant invention.
Figure 3B:
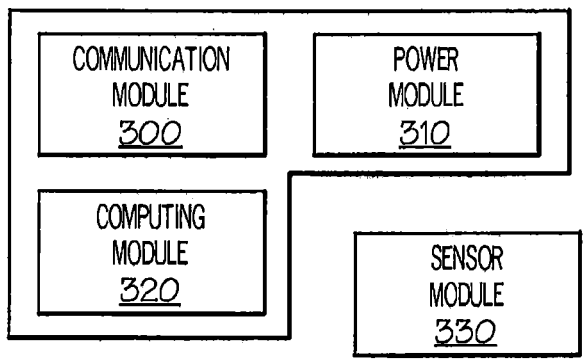
FIG. 3B is a graphical representation a second view of the modularization choices as taught by the instant invention.

FIG. 3 is a graphical representation of the modularization choices as taught by the instant invention. The instant invention teaches a detachable modularized system whereby the entire Mayfunk hardware may be removed from the article of clothing so as to make use of it in another article of clothing. The hardware that is modularized comprises four main modules: a communication module 300, a power module 310, a computing module 320 and a sensor module 330. The invention teaches two modularization choices as shown in FIGS. 3A and 3B. FIG. 3A shows that all four main modules 300-330 are selectively detachable as one large module. FIG. 3B shows that the communication 300, power 310 and computing 320 modules are detachable as one module whilst the sensor unit remains in the article of clothing.

Figure 4:
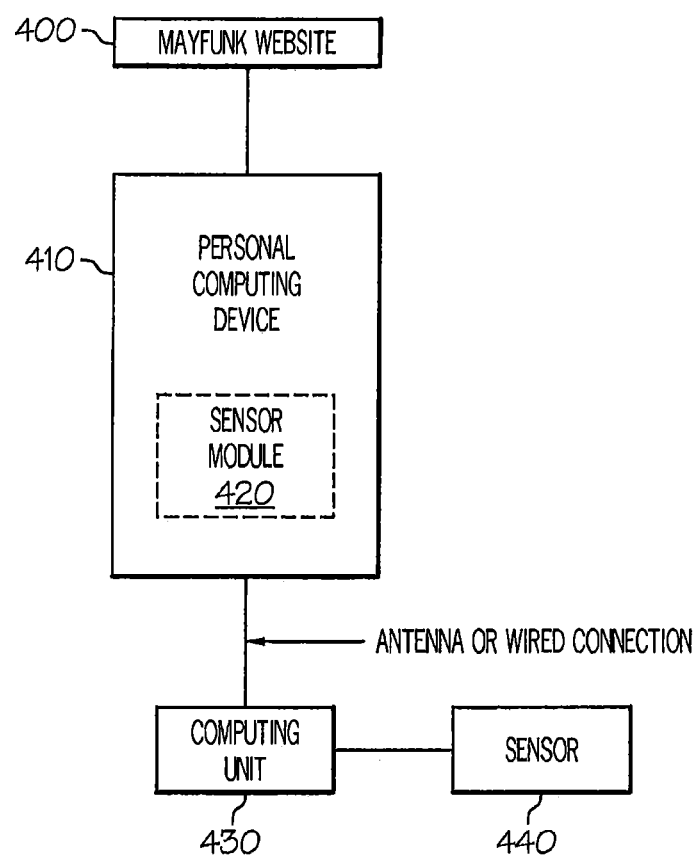
FIG. 4 is a high level illustration of a sports themed website utilized in coordination with the instant invention.

FIG. 4 is a high level illustration of a sports themed Mayfunk Website 40Q utilized in coordination with the instant invention. This drawing depicts a social website (Mayfunk.com for example) so that amateur or professional athletes in one or more sports are enabled to share, compare, socialize, or compete utilizing specific details about their sports. The site has the ability for coaches and or scouts to search for athletes in major metropolitan areas, minor markets and virtually anywhere on the globe. In addition to this, professional and amateur athletes can set up a personal page of the site where they are able to broadcast their personal and statistical information, videos such as YouTube and other audio video performances. Athletes from around the world be able to judge their own performance and determine (according to their age, region, state, country, etc.) where they are in accordance to their performance "bar" for that particular sport or athletic manuever. In order to accomplish all of this, Mayfunk software 420 loaded into a personal computing device 410 (otherwise known as a personal processing unit PPU elsewhere in this disclosure) is programmed to collect and transmit data to the website where the information is digested and visually presented on the website. A sensor 440 measures a quantifiable athletic performance parameter that is transmitted via a bus (not shown) and read into the computing unit 430 that is onboard the article of clothing. This computing unit 430 transmits the sensor data to a personal computing device PPU 410 that digests and processes the sensor information utilizing Mayfunk software 420. Additionally, if the owner of the PPU 410 so desires he or she may forward the athletic sensor data to the Mayfunk website with a few keystrokes, button presses, or touch screen commands.

Figure 5:
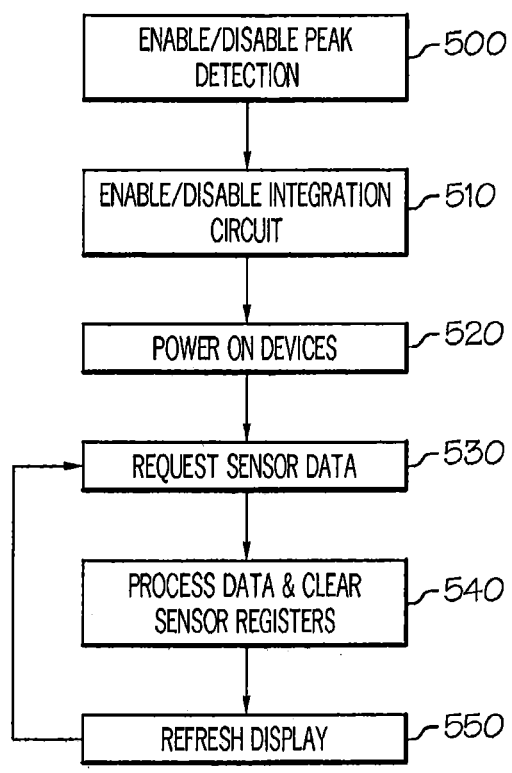
FIG. 5 is a flowchart that shows the operation of the instant invention.

FIG. 5 is a flowchart that shows the operation of the instant invention. It should be understood that an article of clothing contains on/off buttons and one or more mode buttons to set the different scaling functions accessible from the onboard sensors. The routine starts up either through pressing of an on switch located on the article of clothing connected with the circuitry of FIG. 1, or through the inputting of commands to start the sensor data collection utilizing a PPU such as personal computing device 410. The PPU or the buttons on the article of clothing transmits that command to the computing unit 100 onboard the article of clothing to commence ordinary operations. At the start of ordinary operation the software enables peak detection 500 in the event that the appropriate buttons have been pressed on the article of clothing or a command(s) has been received from the PPU; otherwise, this function is disabled. Peak detection indicates the topmost measurement of various parameters such as height, temperature, breathing rate and many other parameters that are amenable to this scaling value. Then step 510 enables an integration circuit so as to integrate the values that are being sensed in the event that the appropriate buttons have been pressed on the article of clothing or a command(s) has been received from the PPU; otherwise, this function is disabled. The integration circuit may also include summing circuits or various other data shaping and analysis equations. Whilst steps 500-510 have utilized peak and integration circuits' enablement it should be understood that this is only a particular exemplary combination. A more generalized example envisions a generic summation function alone or in combination with a detection circuit; further extending this concept allows for the inclusion of one or more other summation and or detection circuitry enablement. After the integration circuits have been enabled in step 510 the device is powered on 520 meaning that the sensor unit is powered on via communication over bus 110. The computing unit 100 requests sensor data utilizing bus 110 to communicate with the sensor unit 120 in step 530. When computing unit 100 receives sensor information across bus 110 it is processed 540 by the onboard computing unit 100 that also clears sensor registers to await the next data value. Finally, the routine refreshes a display (such as an LCD) on the article of clothing with the processed data value so that the owner of the article of clothing can ascertain his current status. This routine continues indefinitely as long as power is supplied to the various components or until a PPU or an off button on the article of clothing is utilized to transmit a stop command.

Figure 6:
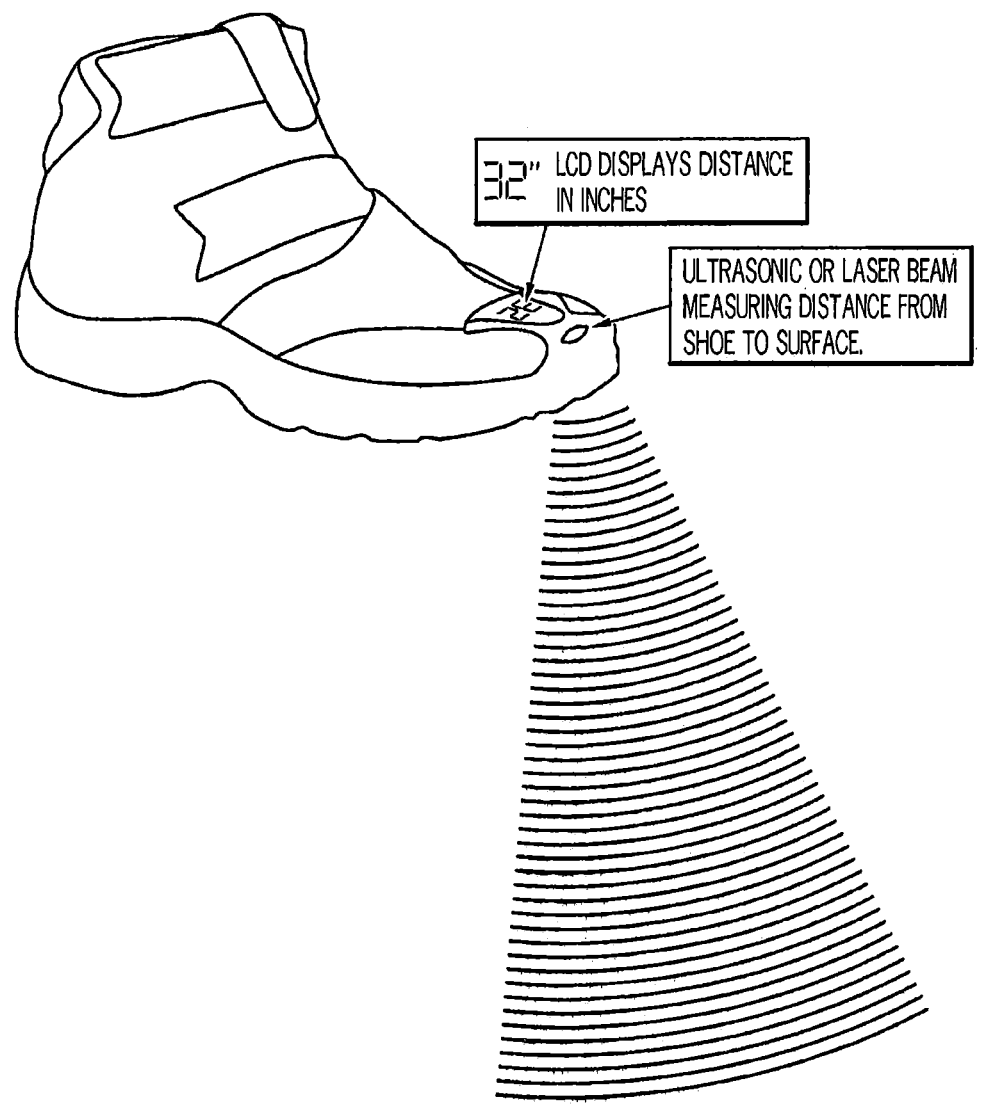
FIG. 6 is a graphical representation depicting a prototypical athletic shoe that incorporates the distance and vertical height measuring technology and LCD display on the footwear itself using the instant invention.

FIG. 6 is a graphical representation depicting a prototypical athletic shoe that incorporates the distance and vertical height measuring technology and LCD display on the footwear itself using the instant invention. Whilst this figure depicts a shoe as an article of clothing, the Mayfunk technology envisions any article of clothing incorporating the appropriate embedded sensor and modularized processing unit along with the associated power, antenna, and bus needed to facilitate the measurement of athletic parameters. The particular example shown has a electromagnetic sensor such as a laser or ultrasonic sensor unit on the sole of the shoe, however, neither the location nor the type of sensor should be viewed as limiting since there are a variety of locations for the sensor to be disposed upon the article of clothing. For example, a glove may have the sensor embedded on the middle part of a finger in the event that it is grasping a golf club whilst a sensor may be placed at the bottom of an athlete's small finger in the event he or she is grasping a baseball bat.

Figure 7:
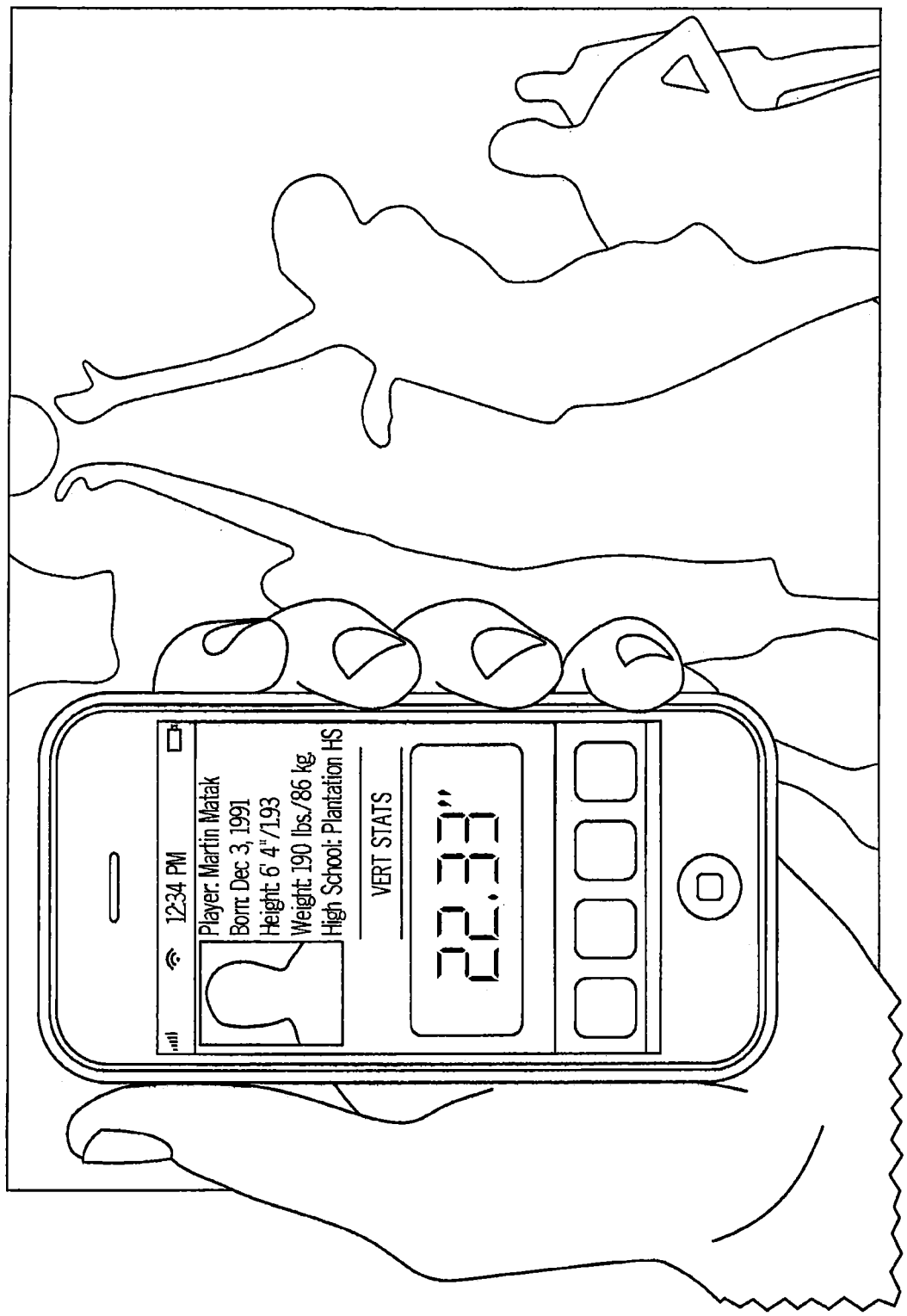
FIG. 7 is a graphical representation depicting the instant invention's vertical measurement displayed on a personal computer device.

FIG. 7 is a graphical representation depicting the instant invention's vertical measurement displayed on a personal computer device as shown in FIG. 4, item 410.

Figure 8:
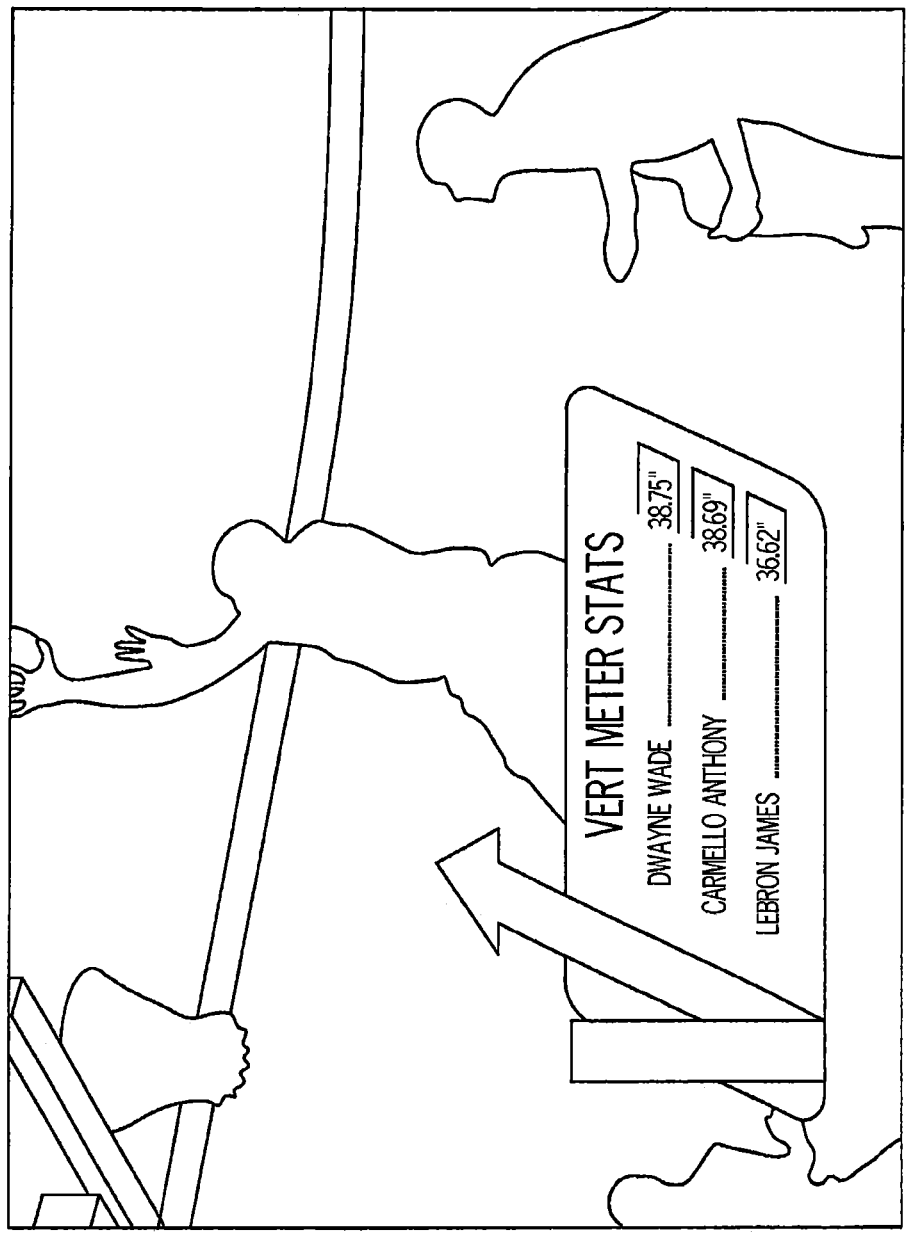
FIG. 8 is a graphical representation of the instant invention's VERT METER™, depicting representative maximum vertical jump heights for different athletes.

FIG. 8 is a graphical representation of the instant invention depicting representative maximum vertical jump heights for different athletes.

Data Transmission Examples a. Sensor to device: Mayfunk sensor transmits data to an external device (Blackberry™, I-Phone™, I-Pod™ etcetera). Mayfunk sensors are incorporated into an article of clothing (shoe, hat, wrist guards, shirt, pants, gloves, socks, shorts, undergarments etcetera) for an athlete. He or she can measure his performance and transmit this data to his personal processing unit (PPU) or other computing device (PDA, cell phone etcetera) as well as viewing this data on an LCD display on his article of clothing. The data can be stored on his PPU, cell phone, Blackberry™, Ipod™ etc.

b. Mayfunk sensor transmits data to a receiver to be broadcast on television. In this case, Mayfunk sensor transmits data to a receiver regarding the specific athletic parameter being measured in real time (called in the prototyping VERT METER™) for viewing at home or in a stadium. In addition, these measurements would be advertised with a specific sponsor endorsement as the statistics are displayed in real time as the game and player results are broadcast during the event.

c. Mayfunk sensor data is uploaded to a website. In this case, PPU data is transmitted or uploaded to Mayfunk.com social website for athletes. The athlete can compete with peers, socialize, analyze his/her performance "bar" data, and compare data results from previous performances and peers.

Original VERT™ Prototype

The original prototype related to athletic shoes or other footwear that integrally comprise vertical jump and or height meters, that measure, record and display the maximum height of a particular jump. The special sensors can be ultrasonic or laser transmitters and processing electronic circuitry which transmit, receive and process the signals with digital or digital/analog conversion technology. Other technologies, such as radio, optical and electromagnetic transmissions of different frequencies including microwaves are also alternatively utilized.

The sensors and ultrasonic transducers can be placed about various locations on the shoe soles, i.e., toe, heel or central area, or about the perimeter of the shoe. The digital display location can vary on the footwear as well. It is contemplated that miniaturized technology having durability, impact and shock-resistant features to protect the sensor and electronic packages and or devices within the base or perimeter of the footwear will optimize performance. The precision selection of appropriate and cost-effective materials and components are to be determined utilizing routine engineering analysis. This would include associated circuit boards, integrated circuits and housings. It can be appreciated that the distance measuring technologies, frequencies desired or required for optimal performance, hardware and software, power sources, battery types and power output will be determined during routine analysis.

Related aspects of the original VERT™ prototype are that once the sensing technologies detect and display the jump height, that same data can be relayed in real time to arena displays, jumbotrons, and televisions for home viewers (such as yellow goal lines in football). Similarly, the data can be input to MP3 players, iPODS™, iPHONES™, Blue Tooth devices, cell phones, PDAs, laptop computers, and other digital multi-media devices or consumer electronics such as displays, as well as televisions, computer monitors, WiFi networks and devices, audio players and similar multimedia devices for receiving the data and providing same to consumers.

The system is a means of providing real time data and information, in the heat of performance and athletic competition, to the athlete, teammates and competitors as well as fans, television viewers and consumers via wireless or wired networks. This is achieved in part through the use of compact or miniaturized electronics, secured and impact resistance components, sensors and displays, and a seamless integration into the shoe wear itself. In this regard, it is appreciated that the fan, reporter, coach or corporate officer can watch the athletic contests and their favorite player, listen and view the players statistics in real time and instantaneously, and monitor the maximum heights of jumps for dunks, "air time", spectacular plays or tip-offs; these statistics are coveted by many fans, fantasy leagues, competitions and gambling purposes amongst others. It is foreseen that such a statistic will approach the significance of time-honored stats such as three-point baskets, field goal percentages, hang-times, and by analogy 40-yard dash times and touchdowns in football. Enhanced graphics would illustrate the vertical leap by arrows, vectors and vivid color schemes, similar to the superimposed first down lines and demarcations for emphasizing relative positions on the field for television viewers during football games.

a. VERT™ Prototypical Devices

VERT™ is Applicant's coined term and proprietary trademark for the novel device and footwear product that can measure the maximum vertical leap (or height) of a person jumping using measuring technology such as ultrasonic/laser technology that is attached to, and incorporated within a shoe. The data from the measuring technology (for example ultrasonic) is calculated by an algorithm program that captures the optimum height or vertical jump and removes all jump anomalies. The jump data (and continuous motion data) will be displayed real time on the athletes shoe via LCD displays and wireless technology. Other aspects are the transmission of the data (for example Blue Tooth devices) that are used to broadcast data to electronic receivers such as cell phones, PDAs, and many different types of consumer electronics or computer devices.

b. VERT™ Wireless Applications

1. Personal use: As an example, an individual athlete during basketball practice will have the ability to capture his/her individual jump shot performance and measure his/her ideal vertical leap height and rate. This can be accomplished by taking a series of 20 similar jump shots and analyzing height ratio vs. shot success allowing the player to apply these statistics in an individual or team practice "my best jump shot percentage is when I hit a 20"VERT™", meaning vertical jump height for a high percentage success rate in making the shot. This "individual performance" will also parallel "team performance" which will allow the coaching staff to adjust and inform players via VERT™ data analysis. Data analysis will become an ongoing tool to measure athlete performance in real time in order to give individuals and teams the winning edge. In addition, VERT™ data analysis will give a player constant awareness of where he/she ranks amongst his/her peer group known as a "bar".

2. Commercial and Entertainment use: real-time broadcasts will allow viewers of a game and/or event the ability to track, analyze, and tout VERT™ data real time in any game/event setting. Two examples of such a broadcast: Little league game: will have the ability to watch your kid's performance via WiFi or cellular technology and phones (like i-PHONE™) and cheer for and root the players' performances as well. Sensor data is collected by the processing unit in the article of clothing and transmitted via the onboard antenna to one or more other processing unit(s). This other processing unit is either for the local display of the athletic statistics or for the forwarding of the sensor data onto another communication media such as the internet, interactive television or some other network. A dedicated server is programmable with Mayfunk software for the collection, formatting and transmission of this data in real time onto the other network. Other advantages and features include "coaching" from the sidelines. NBA/College games: Fans will have the ability to watch and monitor their favorite players' VERT™ stats simultaneously as actions occur and in real time during the game. The fan can monitor performance on their cell phones, electronic device, interactive television or monitor, and/or via jumbotrons, and the top players the game, network or individual selects. The process of transmission to different communication media such as Jumbo-Trons, interactive TV, and or websites, is tied to a central web service. The individual personal units (PPU) communicate via WiFi to a central Vert performance server. WiFi provides inter-operable wireless access between devices. Wi-Fi generally makes access to information between devices from different manufacturers easier, as it can eliminate some of the physical restraints of wiring which can be especially true for mobile devices. Using WiFi, the individual performance units communicate to the aforementioned Vert performance server which in turn streams, downloads or transfers datafeeds based on subscriber preferences to any internet capable device. A corporate or team subscription will have the option of installing a Vert performance server locally with tailored datafeeds for spectators during live events. Further, the ability of real time data will allow the network for College and NBA games to broadcast real-time data for television, cable, satellite and internet viewers as well. Applicant has coined the phrase VERT METER™ for displaying the vertical leap height, player's name, and multi-media presentation.

c. VERT METER™ Marketing and Business Method Applications

VERT METER™ is an application in which a graphical image utilizing VERT™ technology is displayed during a sporting event. In the case of basketball, a VERT METER™ would be endorsed by specific "advertiser" and the VERT™ stats of the game would be displayed in real time as the game (and player) results are posted during broadcast of the event via television, radio and internet. The data from Applicants technology will be beamed real time throughout the event allowing broadcasters and announcers to voice statistical performance for individual and team players. An example of an announcement would be "The VERT METER™ stats of the game are brought to you by Verizon™ . . . . Raising the bar of your performance. Tonight's Verizon VERT™ leader is no other than Dwayne Wade with a 37" VERT™ to end the game with an astonishing and incredible slam-dunk". The instant athletic footwear, sensors, electronic circuitry and technology, along with VERT METER™ marketing and business methodology will add both direct and indirect revenue via participating partners when licensing this wireless technology and utilizing VERT METER™ proprietary intellectual property.

Prototypes

Figure 9:
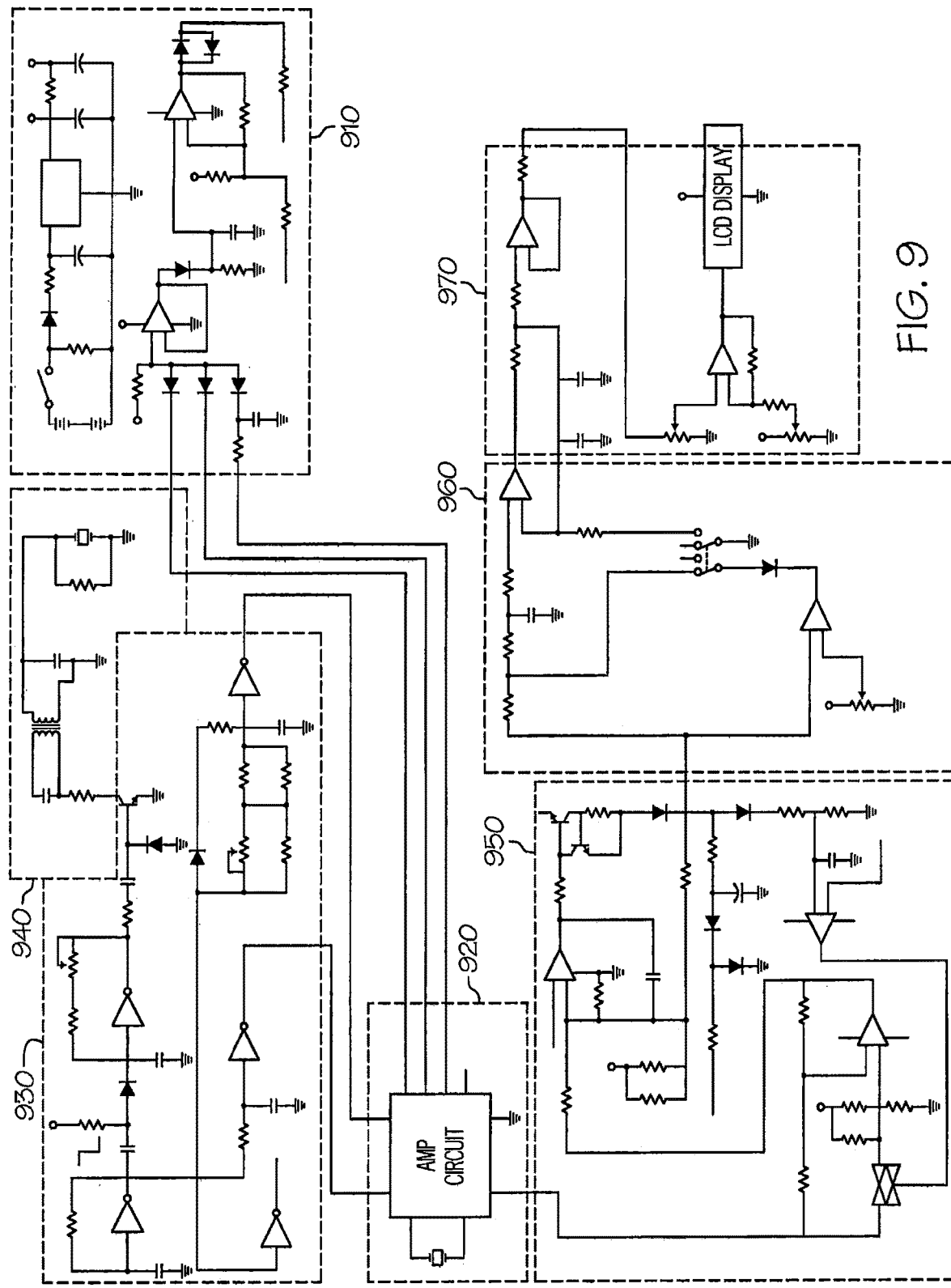
FIG. 9 is an electronic circuit describing the original VERT™ prototype.

Applicant has successfully designed, built and tested prototypes of technology incorporating the instant inventions as described herein. Ultrasonic transducers and sensors manufactured by the Migatron Corp. and Spaleta engineers have been modified and incorporated into athletic footwear per Applicant's specifications and custom designs, as well as in conjunction with LCD displays that indicate jump height. Matters of design choice to one skilled in the art include switches, memory modes, operating temperatures and compensations, beam width and power source, analog output conditions, zero and span range, self-contained sensors, turbulence, vibration and impact conditions, response times and the like. Similarly, electronic processing circuitry, software and calculations used in conjunction with the transmitters and receivers are matters of design choice with varying parameters, accuracy desired and cost-effectiveness of components and materials. One of the prototypes that has been developed has the electronic circuitry as shown in FIG. 9. The following is a short description of the basic functioning of this early prototype. The systems comprises seven basic sub-circuits including: 1) a Power Supply Sub-circuit; 2) a Pulse Timing Sub-circuit; 3) a Pulse Filtering Sub-circuit; 4) a Transmitter Sub-circuit; 5) a Detection Conditioning Sub-circuit; 6) a Peak Detection Sub-circuit; and 7) a Distance Readout Sub-circuit. In the overall circuit of FIG. 9 there are two ultrasonic sensors in use. One is used as a speaker, which sends out short pulses or ultrasonic waves with a preferred frequency. The second acts as a microphone and listens for any reflected ultrasonic signals. The AMP CIRCUIT uses properties of the discharge timing of an RC circuit to record a time delay as a voltage difference. The longer the time the larger the voltage difference that is being compared. If the circuit waits too long, the internal voltage in the RC circuit drops below some minimum threshold, and the timing circuit resets itself and sends out the next pulse. The rest of the circuitry is just additional electronics to either condition the voltages for output or display. Each of the aforementioned sub-circuits are now described in short summaries.

(1) Power Supply Sub-circuit (FIG. 9, 910): Provides on-board battery backed power and regulated voltages for operation (2) Pulse Timing Sub-circuit (FIG. 9, 920):

Measures time delay from between pulse transmission and reception

Output: short voltage pulses to (3) to initiate timing sequence

Input: voltage signal on ultrasonic receiver

Timing sequence completes when input voltage at ultrasonic receiver is high enough.

The minimum voltage is chosen in the circuit design

A new timing sequence is initiated either when an input voltage is recorded or a timeout condition is reached.

(3) Pulse Filtering Sub-circuit (FIG. 9, 930):

Condition the timing pulse from (2) as an acceptable input to ultrasonic receiver circuit (4)

(4) Transmitter Sub-circuit (FIG. 9, 940):

Sets the operational frequency and emits ultrasonic beam. Takes a conditioned timing pulse as input.

(5) Detection Conditioning Sub-circuit (FIG. 9, 950):

Once a timing sequence completes in (2), a voltage signal corresponding to a time delay is passed to (5) for conditioning into a distance measurement.

(6) Peak Detection Sub-circuit (FIG. 9, 960):

Optional sub-circuit that will hold the highest recorded value. This circuit is controlled via a physical switch, used to disable or reset the peak value back to zero.

(7) Distance Readout Sub-circuit (FIG. 9, 970): an input voltage is re-scaled as input for the dedicated LCD readout electronics.

Applicant is in the process of miniaturizing the technology, components, housings and materials to produce a commercially superior and acceptable product line for the instant athletic footwear and electronics.

Applicant deems several aspects of the inventions to be novel, useful, non-obvious and patentable, including novel combinations of technology in the field of footwear, business methods, data compilation and organization, software processes, system design and configuration, amongst others.

The instant description, figures, schematic, charts, and drawings illustrate to one of ordinary skill in the art, how to design, install, implement and utilize the instant athletic footwear which incorporates integral electronic circuitry and components for measuring and displaying vertical jump height and methodology.

Early Technical Abstract of Invention:

The personal athletic performance system is a modular configuration of electronics that is embedded in or attached to sports apparel or sporting equipment to provide quantifiable data telemetry valuable for athletic training or personal performance trending.

The simplest configuration involves a single computing unit that is uploaded with customized software programs depending on the athletic activity. The computing unit comprises a microcontroller, a computer connection interface, and several general-purpose connections to be used to connect to other components of the modular system. The computing unit is meant to be a common reusable element across multiple athletic activities that make use of similar sensor technologies. As new technologies are developed, the computing unit can be upgraded that includes new capabilities but is still backwards compatible with previously purchases athletic sensor sets.

New software is optionally uploaded to the unit via a connection to a personal computer or cellular phone, before a new athletic activity. Though typically a computing unit will come pre-configured for one or more activities as part of the purchase of an activity bundle that includes specially designed apparel or equipment that is meant to use the athletic performance system electronic components. The personal processing unit can be easily removed and reused with other activity bundles.

In this simple configuration, the computing unit collects performance telemetry data from one or more sensors, known collectively as a sensor set. The sensor set is tailored for a specific athletic endeavor. The sensor sets can be made up of a combination of digital or analog devices. They can include electronics that act as sensor input, or they can also include indicators and switches to be used to control the computing unit operation or to provide instant feedback. In the case of a golf-training scenario, a sensor set optionally includes indicator lights for feedback on clubface position or stance balance.

The same computing unit can be re-used with different sensors sets by uploading the corresponding software programs for that sensor set from a personal computing device such as a cellular phone or personal computer. Typically a purchased activity bundle will include apparel or equipment with embedded sensor set electronics.

In the simplest configuration the computing unit is also connected to one or more data communication modules. The communication modules to choose from can include a local display such as an led read out, a data logging device such as a micro-SD card which is later read by a personal computer, or one of many wired or wireless communication options for near-real time transmission to another computing device. Typically, a single communication module is in use and would physically attach to the computing unit. Activity bundles optionally include a communication unit, or they can be purchased separately.

The same power source module energizes the computing unit, sensor set, and communications module. The power module would consist of a rechargeable battery or optionally an external power source such as a USB cable to a computer.

The power module may need to be physically attached to the computing unit, or it may be a physically separated module connected to the personal processing unit only by a wired lead. The exact form factor and voltage needed, is determined by the space, weight and movement constraints of an individual athletic activity. As the system is modular different power module options can be included in different activity bundles or optionally provided a la carte.

The available sensor set configurations can be extended further using radio telemetry technology for sensor situations where a physical connection between the computing unit and sensor is impractical or impossible. Such sensors would need to provide their own power source. An upgraded computing unit may need to be purchased to make use of these radio-based sensors.

The modular system also has the capability to be configured in more complicated situations were multiple computing unit s work together in a meshed network configuration. A mesh capable computing unit s is optionally used in place of the basic computing unit s using the same athletic sensor sets. In such a configuration, each computing unit would make peer wireless connections to nearby units in the mesh in such a way that only one data logging unit or personal computer would be necessary to pull data from any and all computing unit in the mesh network. In this way, the modular athletic performance system can be scaled to include team performance information in a coordinated way. The following are some basic examples of different contemplated configurations. The mentioning of specific components does not disparage the use of other similar devices. For example, the citing of a lithium battery does not limit the applicant to that particular type of device and similarly for the other items.

Basic Athletic Activity Examples

Basic Basketball Bundle:

Activity Specific Sensor Set: Instrumented shoes

Computing unit: Snaps onto back or side of shoe

Communication Module: data logger or LED Display attached to computing unit

Power Module: Lithium Battery attached to computing unit

Shoes:

Embedded range finding technology for vertical jump calculation

Accelerometers for lateral movement

Includes start/stop/reset buttons for interacting with the computing unit

Basic Golf Bundle:

Activity Specific Sensor Set: Instrumented clubs, gloves

Computing unit: Snaps onto back of glove

Communication Module: Bluetooth or data logger attached to computing unit

Power Module: Lithium Battery attached to computing unit

Glove:

Embedded palm and finger tip pressure sensors for grip information.

Includes start/stop/reset buttons for communication with computing unit.

Club:

Embedded accelerometer and pressure sensors in club head for golf swing and ball strike data Embedded compass for clubface direction data.

Club handle provides a wired connection to glove. The connection uses a magnetic coupling, so that if the grip is released on the club the wired connection can disengage without causing damage or injury. (Could be extended with additional sensors into an advanced training package to provide feedback on stance and club grip.)

Figure 10:
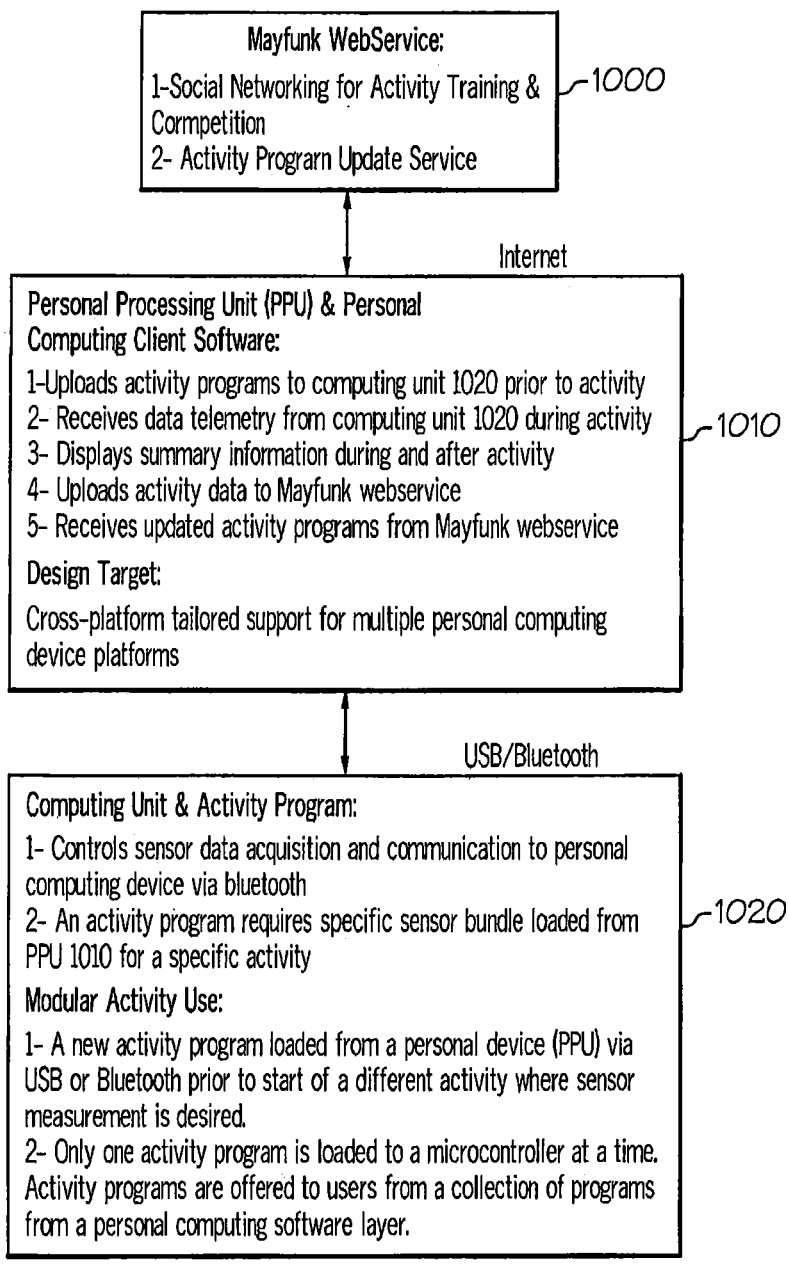
FIG. 10 is an illustration of the overall system including an internet based Mayfunk Webservice.

Basic Cycling Bundle:
Activity Specific Sensor Set: Bicycle accessory pack
Computing unit: attached to bicycle on handlebar
Communication Module: data logger or handle bar LED Display or wireless attached to computing unit
Power Module: Lithium Battery attached to computing unit
Bicycle accessory pack:
RPM sensor attached to bicycle tire
Tilt sensor for incline telemetry
GPS for location
Personal heart rate monitor with magnetic coupling to prevent injury or damage in case of a fall
Includes handlebar start/stop/reset buttons for interacting with the computing unit.
Basic Running Bundle:
Activity Specific Sensor Set: Arm band unit, RF shoe pod
Computing unit: Attached to arm band.
Communication Module: data logger or LED Display or wireless attached to computing unit
Power Module: Lithium Battery attached to computing unit
Armband:
GPS
Heart Rate Monitor, using magnetic couplers
radio receiver antenna to communicate with shoe pod
control buttons to use with computing unit
Shoe Pod:
accelerometer for stride cadence information
pressure sensor for footfall
radio transmitter
on/off switch
Basic Curling Bundle:
Activity Specific Sensor Set: shoes, glove, broom, belt
Computing unit: attached to waist
Communication Module: data logger or LED Display or wireless attached to computing unit
Power Module: Lithium Battery attached to computing unit
Shoes:
pressure sensors for push off when throwing, provides balance and power information
wired connection under clothing to computing unit at waist, using magnetic coupling for safety
Glove:
accelerometer and tilt sensor for hand position information during throwing
Wired connection under clothing to computing unit at waist
Broom:
pressure sensor and accelerometer information concerning sweep speed and power
Wired connection to glove using magnetic coupling
System Overview including Mayfunk Webservice:
FIG. 10 is an illustration of the overall system including an Internet based Mayfunk.com Webservice. The Mayfunk.com WebService 1000 comprises a Social Networking for Activity Training & Competition software architecture; this provides interactive subscriber communication including the loading, storage and retrieval of athletic statistics to and from the hardware and software supporting the webservice 1000. Subscribers are thereby able to share their performance parameters as well as the performance statistics of famous athletes with friends on a real-time and after hours basis. Thus, the Mayfunk.com webservice 1000 makes it possible to share stats by uploading and downloading stats during live athletic competition such as professional or semi-professional sports as well as local adolescent leagues. Further, an easily accessible webpage is programmed for the manual uploading, downloading and storage of athletic statistics that are transmitted from the various athletic sensors present on an athlete's clothing.

In other words, an athlete can use his or her PPU to monitor his or her statistics associated with Mayfunk sensors or those of his friends and manually input this data through the use of a webpage programmed for entry of this data. By accessing the internet in a conventional manner, an individual may enter the data manually by typing it into the webpage; he or she may optionally transfer the data by plugging the PPU into a (USB wired, Bluetooth wireless etc. . . . ) computer port and loading the file into the webservice across the internet with a simple data transfer command using pre-existing communication protocols. The reverse procedure is also programmed into the Mayfunk.com webservice software and client computing software; in other words, using a webpage to manually retrieve data from the online storage database as well as the loading of a PPU through a wired or wireless connection to an internet capable computer. Alternatively, the webservice is also programmed for automatic storage of data that bypasses the webpage itself. For example, during individual or team play, various performance statistics from one or more athletes equipped with Mayfunk computing and sensor devices are sent automatically via the Internet for automatic storage in the webservice. In this manner, the system provides for real-time automated storage of athletic stats as well as manual storage and retrieval of the data entered into the webpage. The automated retrieval of athletic performance parameters is also contemplated by applicant; here, subscribers automatically receive real-time or delayed stats according to their user selected or preprogrammed user preferences into their PPU for selected athletic events or for a set of events suggested by the Mayfunk.com webservice. For example, the service polls first time users or at other predetermined times for the type of athletic events a user might want. If a user selects professional tennis and or a sub category of tennis competitions then this category is streamed to the user's PPU at the time of the competition or the next time the PPU is activated. It should be finally noted that all of the automated and or manual decisions can alternatively decided on an event by event basis leaving the question open until the user makes a decision.

The aforementioned functionalities are made possible through the use of Personal Computing Client Software loaded onto a subscriber's Personal Processing Unit 1010 (PPU). This computing software is updated via an Activity Program Update Service associated with the Mayfunk.com Webservice. The updates are optionally initiated automatically via a preprogrammed or pre-selected time frame or updated by a user activation request for it. User activation of the program update service is governed via the default personal computing client software loaded into the PPU 1010 that presents a user of the PPU a series of choices to a) start the software update; b) select time period updates or c) accept a default update time.

As has been discussed previously, the Personal Processing Unit (PPU) 1010 is a device such as an IPOD™, an IPhone™, a PDA, a Blackberry™, a cell phone, an MP3 player, a calculator or some other generic hand held electronic device. This PPU interacts with the Internet for the manual as well as automatic reception and transmission of athletic statistics from the webservice and for the communication with the computing unit 1020 that controls a Mayfunk sensor or array of sensors. In order to communicate with these sensors and to operate them effectively, a set of software controls are necessary for each sensor type. The PPU 1010 is preloaded with a personal computing client software to upload activity programs to computing unit 1020 prior to its activation. Once any activity program uploads are complete, data telemetry is received from computing unit 1020 controlling the activated one or more sensors. Additionally, each of the PPUs is equipped with software that permits the display on a graphical user interface GUI associated with the PPU of summary information during and after the athletic activity. The PPU 1010 is then able to upload athletic activity data via the Internet to the Mayfunk-.com webservice 1000 either automatically or through manual activation by user control. When a user originally activates his or her subscription, the user is presented with the option of accepting predefined default periodic data transfers or making the transfers manually or leaving the question open for each event.

There also comes a time for software loaded into the computing unit 1020 to be updated. These updates may arrive for a variety of reasons but principally are changes in existing sensor software that are necessary in order to improve the sensing of the data. Alternatively, the updates are cause by the changing of modules in a sensor package necessitating new software in the computing unit 1020. When a user desires to have a different type of sensor or new sensor module to monitor his or her stats or those of another individual an update to the activity program(s) is necessary for data acquisition to function accordingly. In this event, the Mayfunk.com webservice provides automated or manual updated activity programs that are transmitted to the PPU 1010 of a user. The user is then able to receive updated software for the computing unit 1020 so as to permit the accurate and efficient control and data acquisition associated with the appropriate sensor unit(s).

The Mayfunk.com webservice is able to determine the necessary updated activity program(s) by periodically polling of the PPUs connected to it so as to discern the type of sensor activity programs necessary for each PPU. Alternatively, the updated activity program(s) are requested of the Mayfunk webservice via a request from the Personal Computing Client Software (PPU) 1010 that determines the need for updated software based upon a transmitted update request across the internet containing the current software version loaded in the computing unit 1020.

It is this computing unit 1020 that contains an activity program that controls sensor data acquisition. The activity program also controls communication to personal processing unit PPU 1010 via wired or wireless communication (such as USB or Bluetooth). The activity program requires a specific sensor bundle loaded from PPU 1010 for a specific activity. Whenever a new activity requires a different type of sensor unit, a new activity program is loaded into the computing unit 1020 from a personal processing unit (PPU) 1010 sent from the Mayfunk.com webservice 1000 via USB or Bluetooth prior to the start of a different activity where sensor measurement is desired. Finally, the system permits only one activity program loaded into a microcontroller at a time and that the activity programs are offered to users from a collection of programs from a personal computing software layer.

The initial design target language for the computing unit 1020 are ATMEGA8 and ATMEGA168 microcontrollers: AVR-C or Arduino type. The current software loader is a dedicated microcontroller boot loader that provides re-programmability via USB or Bluetooth (wired or wireless). Initial design target for ATMEGA8 and ATMEGA168 microcontrollers: open source Arduino boot loader: http://arduino.cc/en/hacking/bootloader.

Transmission to different communication media (Jumbo Trons, interactive t.v, web sites):

This functionality is tied to the central webservice. The individual computing units communicate via wifi to a central Vert performance server, that then streams datafeeds based on subscriber preferences to any internet capable device. A corporate or team subscription will have the option of installing a Vert performance server locally with tailored datafeeds for spectators during live events.

Finally, it should be understood that the Mayfunk software that has been described and throughout this document are cross-platform tailored with support for multiple personal computing device platforms.

Figure 11A:
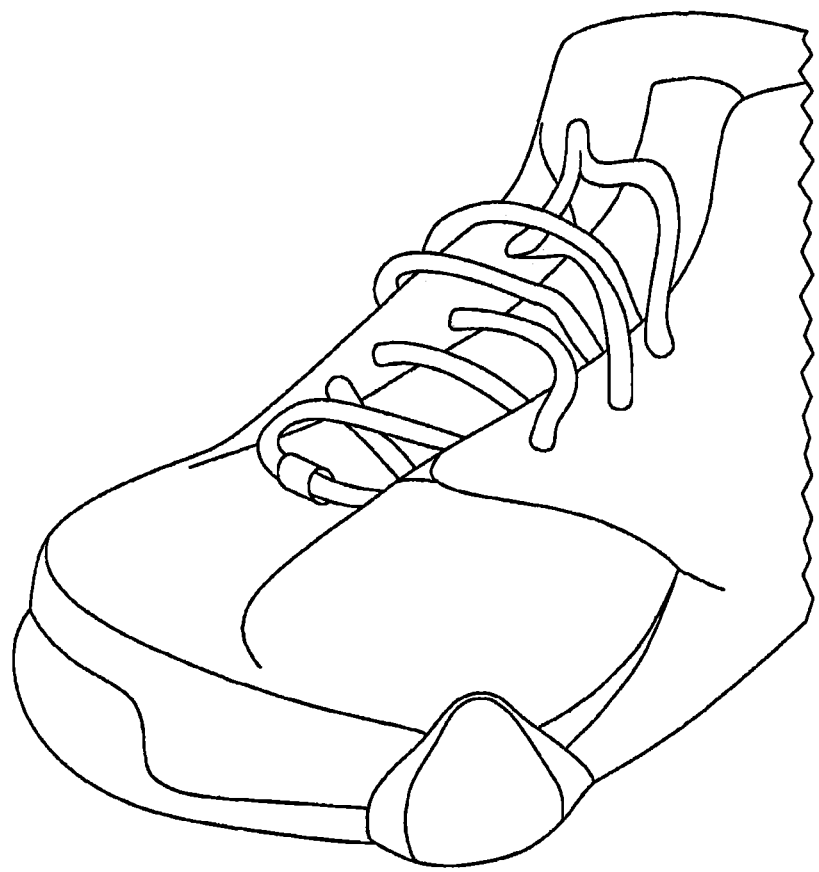
FIG. 11A illustrates the mounting of a sensor on a shoe as viewed from the top of the shoe.
Figure 11B:
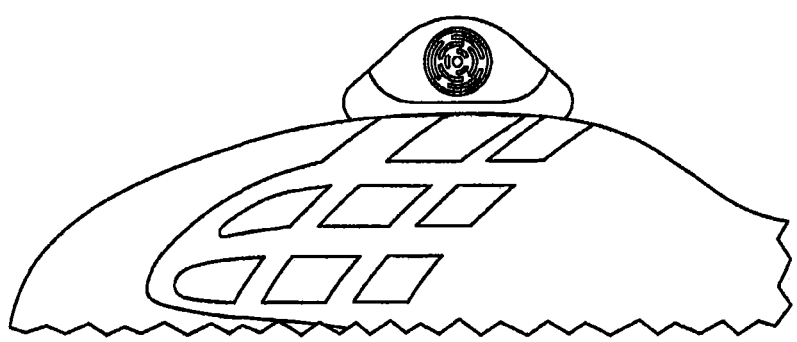
FIG. 11B illustrates the mounting of a sensor on a shoe as viewed from the bottom of the shoe.
Figure 12A:
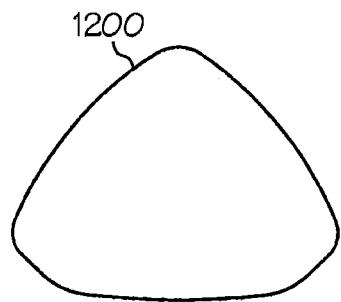
FIG. 12A illustrates a first view of a sensor component which is part of a sensor and bracket configuration for the Mayfunk hardware.
Figure 12B:
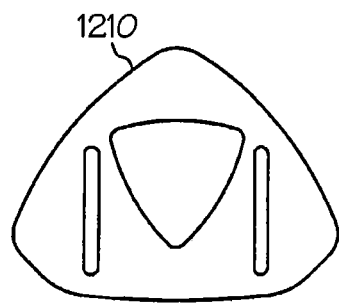
FIG. 12B illustrates a second view of a sensor component which is part of a sensor and bracket configuration for the Mayfunk hardware.
Figure 12C:
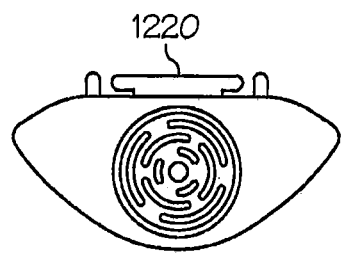
FIG. 12C illustrates a third view of a sensor component which is part of a sensor and bracket configuration for the Mayfunk hardware.
Figure 12D:
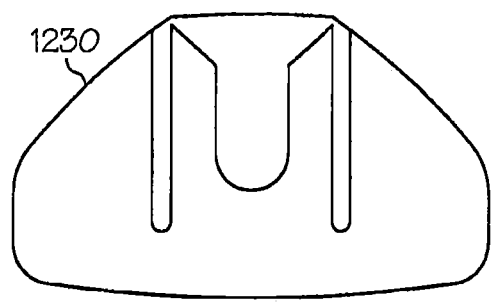
FIG. 12D illustrates a first view of a bracket component which is part of a sensor and bracket configuration for the Mayfunk hardware.
Figure 12E:
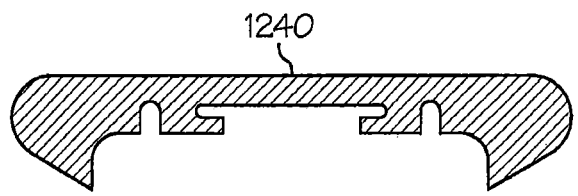
FIG. 12E illustrates a second view of a bracket component which is part of a sensor and bracket configuration for the Mayfunk hardware.

FIGS. 11-12 illustrate the mounting of a sensor on a shoe and a sensor and bracket configuration for the Mayfunk hardware.

Specifically, FIG. 12 illustrates the sensor unit and bracket in items 1200-1240. The Mayfunk sensor is shown in items 1200-1220 while the Mayfunk bracket is shown in items 1230-1240. The Mayfunk sensor is shown in its front view 1200 along with associated logo and its back view 1210 describes protrusions (lines and dark triangle area) that are integral with the sensor unit and extend off the ordinary surface of the light triangular area of the sensor unit. These protrusions are to be inserted into the bracket as a male connector is inserted into the female connector bracket shown in 1230-1240. The sensor's back view is shown in item 1220 along with a mounting bracket male connector in the top of the figure; this mounting bracket male connector is to be inserted in the slot of the female bracket of 1230-1240. Item 1230 shows the bracket front view mounting clip-in slot that serves as the receiver for the sensor unit protrusions described with respect to items 1200-1220. Item 1240 shows the bracket top view and more clearly illustrates the mounting clip in-slot for receiving the male connector piece. As shown in this example, the bracket is attached to a shoe with an adhesive and the sensor unit is attached to the bracket with a simple male-female snap in connector configuration. However, other attachment configurations are possible such as the physical integration of the sensor unit into the shoe as one piece with the shoe without mounting on a bracket. Also, whilst a shoe has been shown as the piece of clothing that has the Mayfunk technology, it is contemplated by the inventor that any ordinary piece of clothing may be adapted to incorporate the Mayfunk sensor, power supply, computing unit and any future add-ons. These pieces of clothing such as a shirt, shoe, cap, socks, shorts, pants, gloves, hat (etc) have similar mounting brackets with the instant invention's technology attached thereto. Additionally, the entire system may be made integral with the article(s) of clothing such that it is not easily identifiable to an external user providing no performance penalties for the use of the device(s); this is accomplished by using common materials (plastics, rubbers, linens, cottons, polyesters, etc) used in the manufacture of the device to mount, shroud and or disguise the device(s) as part of the article(s) of clothing. In either case, whether overtly displayed or covertly worn the Mayfunk devices are designed to be fully detachable, partially detachable, or non-detachable thus running the full range of potential options. Other modifications to the mounting bracket system are described as follows.

Figure 13A:
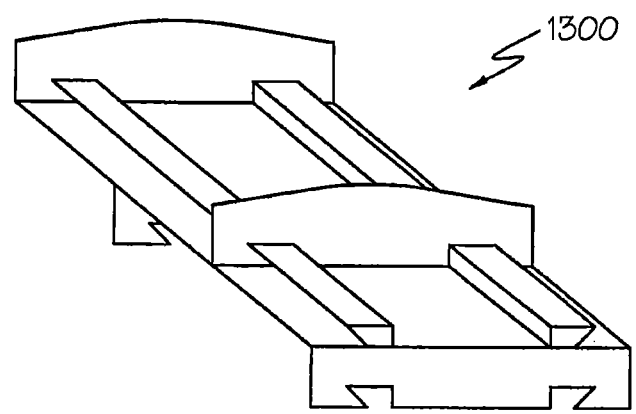
FIG. 13A shows a perspective view of a tongue and groove locking electro-mechanical connections along with stackable add-ons.
Figure 13B:
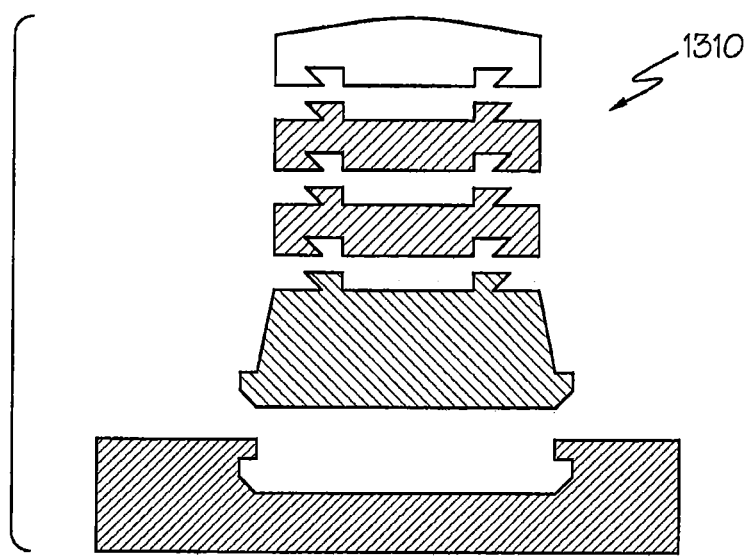
FIG. 13B shows an exploded cross-sectional view of a tongue and groove locking electro-mechanical connections along with stackable add-ons.

FIG. 13 items 1300 and 1310 shows a tongue and groove locking electro-mechanical connections along with stackable add-ons. Specifically, item 1300 shows a tongue and groove connection where the tongue and groove rails contain the electrical connections for the hardware. Item 1310 describes how the tongue and groove connections provide stackable add-ons with an electrical connection to the mounting bracket. In this drawing, the athletic sensor(s) are embedded in the piece of athletic clothing (not shown) and a Mayfunk computing unit attaches to the bracket whilst stackable add-ons provide further capabilities and updates to the existing hardware all capped off with a battery for easy replacement. Whilst the sensors have been described as being embedded in the piece of athletic clothing, they may also be contained in one of the stackable add-ons.

We claim:

1. A computer implemented method comprising:
   receiving, during a sporting event, a first batch of raw data at a processor connected to a fantasy sports league network or gambling network, wherein the raw data includes one or more athletic performance parameters that correspond to a physical movement of an athlete;
   computing in real time at the processor, during the sporting event, one or more performance assessments for the athlete based on the one or more athletic performance parameters, wherein the one or more performance assessments correspond specifically to an activity of the sporting event; and
   transmitting, during the sporting event, a first signal from the processor to one or more subscriber devices connected to the fantasy sports league network or the gambling network, wherein the first signal enables a display of the one or more performance assessments or athletic performance parameters on the subscriber devices.

2. The method of claim 1, further comprising receiving a subscriber preference selection from the subscriber device at the processor after receiving the first batch of raw data, and receiving a second batch of raw data at the processor after receiving the subscriber preference.

3. The method of claim 1, further comprising receiving a subscriber preference selection from the subscriber device at the processor prior to receiving the first batch of raw data at the processor.

4. The method of claim 1, wherein the one or more performance assessments indicate at least a peak athletic performance parameter for the athlete.

5. The method of claim 1, wherein the first signal specifies multimedia corresponding to at least one of the one or more performance assessments.

6. The method of claim 1, wherein the first signal specifies multimedia comprising an advertisement representing a sponsor endorsement of the athlete.

7. The method of claim 5, wherein:
   transmitting the first signal comprises using a web service that runs on a server system; and
   the web service permits users associated with the subscriber devices to download the first signal.

8. The method of claim 5, wherein the first signal is downloaded to a subscriber of the fantasy sports league network or a subscriber of the gambling network.

9. The method of claim 1, further comprising:
   providing, for output to a display device associated with the sporting event during the sporting event, a second signal (i) enabling display of the one or more performance assessments on the display device, and (ii) instructing a server to specify multimedia corresponding to at least one of the one or more performance assessments.

10. The method of claim 1, wherein the first signal enables competition over the fantasy sports league network or gambling network.

11. The method of claim 1, wherein the first signal informs one or more subscribers of the fantasy sports league network or gambling network of a result of the one or more performance assessments or athletic performance parameters.

12. A computer implemented method comprising:
    receiving, during a sporting event, a first signal at a processor connected to a fantasy sports league network or a gambling network, wherein the first signal includes one or more performance assessments for an athlete, computed in real time based on one or more athletic performance parameters that correspond to a physical movement of the athlete, wherein the one or more performance assessments correspond specifically to an activity of the sporting event; and
    transmitting, during the sporting event, a second signal from the processor to one or more subscriber devices connected to the fantasy sports league network or the gambling network, wherein the second signal enables a display of the one or more performance assessments or athletic performance parameters on the subscriber devices.

13. The method of claim 12, further comprising receiving a subscriber preference selection from the subscriber device at the processor after receiving the first signal and receiving a third signal at the processor after receiving the subscriber preference, wherein the third signal includes one or more performance assessments for an athlete, computed in real time based on one or more athletic performance parameters that correspond to a physical movement of the athlete.

14. The method of claim 12, further comprising receiving a subscriber preference selection from the subscriber device at the processor prior to receiving the first signal at the processor.

15. The method of claim 12, wherein the one or more performance assessments indicate at least a peak athletic performance parameter for the athlete.

16. The method of claim 12, wherein the second signal specifies multimedia corresponding to at least one of the one or more performance assessments.

17. The method of claim 12, wherein the second signal specifies multimedia comprising an advertisement representing a sponsor endorsement of the athlete.

18. The method of claim 16, wherein:
    transmitting the second signal comprises using a web service that runs on a server system; and
    the web service permits users associated with the subscriber devices to download the second signal.

19. The method of claim 16, wherein the second signal is downloaded to a subscriber of the fantasy sports league network or a subscriber of the gambling network.

20. The method of claim 12, further comprising:
    providing, for output to a display device associated with the sporting event during the sporting event, a third signal (i) enabling display of the one or more performance assessments on the display device, and (ii) instructing a server to specify multimedia corresponding to at least one of the one or more performance assessments.

21. The method of claim 12, wherein the second signal enables competition over the fantasy sports league network or gambling network.

22. The method of claim 12, wherein the second signal informs one or more subscribers of the fantasy sports league network or gambling network of a result of the one or more performance assessments.

23. A computer implemented method comprising:
receiving, during a sporting event, a first batch of sensor data at a processor connected to a fantasy sports league network or a gambling network;
computing in real time at the processor, during the sporting event, one or more athletic performance parameters that correspond to a physical movement of an athlete;
computing in real time at the processor, during the sporting event, one or more performance assessments for the athlete based on the one or more athletic performance parameters, wherein the one or more performance assessments correspond specifically to an activity of the sporting event; and
transmitting, during the sporting event, a first signal from the processor to one or more subscriber devices connected to the fantasy sports league network or the gambling network, wherein the first signal enables a display on the subscriber devices.

24. The method of claim 23, further comprising receiving a subscriber preference selection from the subscriber device at the processor after receiving the first batch of sensor data, and receiving a second batch of sensor data at the processor after receiving the subscriber preference.

25. The method of claim 23, further comprising receiving a subscriber preference selection from the subscriber device at the processor prior to receiving the first batch of sensor data at the processor.

26. The method of claim 23, wherein the one or more performance assessments indicate at least a peak athletic performance parameter for the athlete.

27. The method of claim 23, wherein the processor comprises a server or smart device.

28. The method of claim 23, wherein the display shows the one or more performance parameters.

29. The method of claim 23, wherein the display shows the one or more performance assessments.

30. The method of claim 23, wherein the first signal specifies multimedia corresponding to at least one of the one or more performance assessments.

31. The method of claim 23, wherein the first signal specifies multimedia comprising an advertisement representing a sponsor endorsement of the athlete.

32. The method of claim 30, wherein:
transmitting the first signal comprises using a web service that runs on a server system; and
the web service permits users associated with the subscriber devices to download the first signal.

33. The method of claim 30, wherein the first signal is downloaded to a subscriber of the fantasy sports league network or a subscriber of the gambling network.

34. The method of claim 23, further comprising:
providing, for output to a display device associated with the sporting event during the sporting event, a second signal (i) enabling display of the one or more performance assessments on the display device, and (ii) instructing a server to specify multimedia corresponding to at least one of the one or more performance assessments.

35. The method of claim 23, wherein the first signal enables competition over the fantasy sports league network or gambling network.

36. The method of claim 23, wherein the first signal informs one or more subscribers of the fantasy sports league network or gambling network of a result of the one or more performance assessments or athletic performance parameters.

37. A computer implemented method comprising:
receiving, during a sporting event, a first batch of pre-processed sensor data at a processor connected to a fantasy sports league network or a gambling network;
computing in real time at the processor, during the sporting event, one or more athletic performance parameters that correspond to a physical movement of an athlete;
computing in real time at the processor, during the sporting event, one or more performance assessments for the athlete based on the one or more athletic performance parameters, wherein the one or more performance assessments correspond specifically to an activity of the sporting event; and
transmitting, during the sporting event, a first signal from the processor to one or more subscriber devices connected to the fantasy sports league network or the gambling network, wherein the first signal enables a display on the subscriber devices.

38. The method of claim 37, further comprising receiving a subscriber preference selection from the subscriber device at the processor after receiving the first batch of pre-processed sensor data, and receiving a second batch of pre-processed sensor data at the processor after receiving the subscriber preference.

39. The method of claim 37, further comprising receiving a subscriber preference selection from the subscriber device at the processor prior to receiving the first batch of pre-processed sensor data at the processor.

40. The method of claim 37, wherein the one or more performance assessments indicate at least a peak athletic performance parameter for the athlete.

41. The method of claim 37, wherein the processor comprises a server or smart device.

42. The method of claim 37, wherein the display shows the one or more performance parameters.

43. The method of claim 37, wherein the display shows the one or more performance assessments.

44. The method of claim 37, wherein the first signal specifies multimedia corresponding to at least one of the one or more performance assessments.

45. The method of claim 37, wherein the first signal specifies multimedia comprising an advertisement representing a sponsor endorsement of the athlete.

46. The method of claim 44, wherein:
transmitting the first signal comprises using a web service that runs on a server system; and
the web service permits users associated with the subscriber devices to download the first signal.

47. The method of claim 44, wherein the first signal is downloaded to a subscriber of the fantasy sports league network or a subscriber of the gambling network.

48. The method of claim 37, further comprising:
providing, for output to a display device associated with the sporting event during the sporting event, a second signal (i) enabling display of the one or more performance assessments on the display device, and (ii) instructing a server to specify multimedia corresponding to at least one of the one or more performance assessments.

49. The method of claim 37, wherein the first signal enables competition over the fantasy sports league network.

50. The method of claim 37, wherein the first signal informs one or more subscribers of the fantasy sports league network or gambling network of a result of the one or more performance assessments or athletic performance parameters.

* * * * *